US009136185B2

(12) United States Patent
Shi et al.

(10) Patent No.: US 9,136,185 B2
(45) Date of Patent: Sep. 15, 2015

(54) METHODS AND SYSTEMS FOR GRAIN SIZE EVALUATION OF MULTI-CYSTALLINE SOLAR WAFERS

(75) Inventors: Gang Shi, O'Fallon, MI (US); Thomas E. Doane, Troy, MI (US); Steven L. Kimbel, St. Charles, MI (US); Robert H. Fuerhoff, St. Charles, MI (US)

(73) Assignee: MEMC Singapore Pte., Ltd., Singapore (SG)

( * ) Notice: Subject to any disclaimer, the term of this patent is extended or adjusted under 35 U.S.C. 154(b) by 579 days.

(21) Appl. No.: 13/329,914

(22) Filed: Dec. 19, 2011

(65) Prior Publication Data

US 2013/0156293 A1 Jun. 20, 2013

(51) Int. Cl.
| | |
|---|---|
| G06K 9/00 | (2006.01) |
| G06K 9/40 | (2006.01) |
| G06K 9/32 | (2006.01) |
| H01L 21/66 | (2006.01) |
| G01N 21/95 | (2006.01) |
| G01N 21/88 | (2006.01) |

(52) U.S. Cl.
CPC ............ *H01L 22/12* (2013.01); *G01N 21/8806* (2013.01); *G01N 21/9501* (2013.01); *H01L 2924/0002* (2013.01)

(58) Field of Classification Search
USPC .......................... 382/145, 266, 294
See application file for complete search history.

(56) References Cited

U.S. PATENT DOCUMENTS

| | | | | |
|---|---|---|---|---|
| 5,757,474 | A * | 5/1998 | Sopori et al. ................. | 356/72 |
| 6,882,739 | B2 * | 4/2005 | Kurtz et al. ................... | 382/109 |
| 8,213,704 | B2 * | 7/2012 | Peterson et al. .............. | 382/145 |
| 2002/0196338 | A1 | 12/2002 | Tham | |
| 2004/0184021 | A1 * | 9/2004 | Lim ............................. | 355/72 |
| 2006/0274931 | A1 * | 12/2006 | Svidenko et al. ............. | 382/145 |
| 2009/0092290 | A1 * | 4/2009 | Rowe ........................... | 382/115 |
| 2009/0281753 | A1 | 11/2009 | Noy | |
| 2010/0194895 | A1 * | 8/2010 | Steinberg et al. ............. | 348/187 |
| 2010/0220186 | A1 * | 9/2010 | Chan ............................ | 348/126 |

(Continued)

FOREIGN PATENT DOCUMENTS

| | | |
|---|---|---|
| DE | 19914115 A1 | 11/1999 |
| DE | 102007010516 A1 | 9/2008 |

OTHER PUBLICATIONS

International Search Report and Written Opinion of the International Searching Authority mailed on Mar. 5, 2013 regarding PCT/SG2012/000482 filed on Dec. 19, 2012; 11 pgs.

(Continued)

*Primary Examiner* — Kathleen Y Dulaney
(74) *Attorney, Agent, or Firm* — Armstrong Teasdale LLP

(57) ABSTRACT

Methods and systems for evaluation of wafers are disclosed. One example method includes illuminating a multi-crystalline wafer according to a plurality of lighting parameters, capturing a plurality of images of the multi-crystalline wafer, stacking and projecting the plurality of images to generate a composite image, analyzing the composite image to identify one or more grains of the multi-crystalline wafer, and generating a report based on the analysis of the composite image. The multi-crystalline wafer is illuminated according to a different one of the plurality of lighting parameters in at least two of the plurality of images.

20 Claims, 7 Drawing Sheets

(56) References Cited

U.S. PATENT DOCUMENTS

| | | | |
|---|---|---|---|
| 2010/0266196 A1* | 10/2010 | Kasahara et al. | 382/149 |
| 2011/0025839 A1* | 2/2011 | Trupke et al. | 348/87 |
| 2011/0268344 A1* | 11/2011 | Chan | 382/145 |
| 2012/0104255 A1* | 5/2012 | Wang et al. | 250/330 |
| 2013/0100275 A1* | 4/2013 | Degreeve et al. | 348/87 |
| 2013/0129187 A1* | 5/2013 | Maxwell | 382/141 |

OTHER PUBLICATIONS

Einhaus, Roland et al., Monitoring of mc-Silicon ingot crystallisation process by optical characterisation of grain size distribution on wafer level, Article, Jun. 2009, 3rd International Workshop on Crystalline Silicon Solar Cells, SINTEF/NTNU, Trondheim Norway, 4 pages.

* cited by examiner

OPTICAL IMAGE

PROCESSED IMAGE

GRAINS REVEALED

METHODS AND SYSTEMS FOR GRAIN SIZE EVALUATION OF MULTI-CYSTALLINE SOLAR WAFERS

FIELD

This disclosure relates generally to multi-crystalline solar wafers and, more specifically, to methods and systems for grain size evaluation of multi-crystalline solar wafers.

BACKGROUND

Multi-crystalline silicon is commonly produced in the form of ingots that are then cut into wafers for, among other things, use in the production of photovoltaic (PV) cell and PV module production. The quality of multi-crystalline silicon, e.g., how well it will perform, is influenced by numerous factors during the production of the multi-crystalline silicon. Various parameters of multi-crystalline silicon may be evaluated as part of the evaluation of the quality of multi-crystalline silicon. One parameter that is sometimes examined is the size and distribution of grain in a wafer of multi-crystalline silicon.

Grain size evaluation is commonly performed by visual inspection. Samples of a multi-crystalline silicon wafer are visually inspected and the number of grains intercepting a line drawn on the wafer are manually counted. Such manual inspection is a time consuming and cumbersome procedure susceptible to human error. At least one known method of inspecting multi-crystalline silicon wafers involves scanning a wafer from various heights, converting the scanned images to black and white images, and having a computer count the number of grains in each image. The cumulative percentage share of occupation of the wafer's surface by different grain sizes and/or average grain size is then calculated. Such known methods and systems are unsatisfactory due to susceptibility to human error, mechanical complications, and other issues. Accordingly, a better method and system is needed.

This Background section is intended to introduce the reader to various aspects of art that may be related to various aspects of the disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

SUMMARY

An aspect is directed to a system for evaluating multi-crystalline wafers. The system includes an imaging apparatus and a computing device coupled to the imaging apparatus. The computing device includes a processor and a non-transitory computer readable medium coupled in communication with the processor and containing instructions. The instruction, when executed by the processor, causes the processor to capture a plurality of images of a multi-crystalline wafer in the imaging apparatus, stack and project the plurality of images to generate a composite image, analyze the composite image to identify one or more grains of the multi-crystalline wafer, and generate a report based on the analysis of the composite image. At least two of the plurality of images are illuminated in the imaging apparatus in accordance with different lighting parameters.

According to another aspect, a method for use in evaluating a multi-crystalline wafer includes illuminating a multi-crystalline wafer according to a plurality of lighting parameters, capturing a plurality of images of the multi-crystalline wafer, stacking and projecting the plurality of images to generate a composite image, analyzing the composite image to identify one or more grains of the multi-crystalline wafer, and generating a report based on the analysis of the composite image. The multi-crystalline wafer is illuminated according to a different one of the plurality of lighting parameters in each of the plurality of images.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

Corresponding reference characters indicate corresponding parts throughout the several views of the drawings.

DETAILED DESCRIPTION

The embodiments described herein generally relate to multi-crystalline solar wafers. More specifically embodiments described herein relate to methods and systems for grain size evaluation of multi-crystalline wafers that can be integrated into solar modules, among other possible uses or applications. The methods and systems may be applied to characterize the grain size of any material with a flat surface on which grain boundaries can be highlighted by etching or other suitable methods. Although generally described herein with respect to multi-crystalline silicon wafers, the methods and systems described herein may be applied to multi-crystalline wafers made of any suitable material including, for example, germanium.

Figure 1:
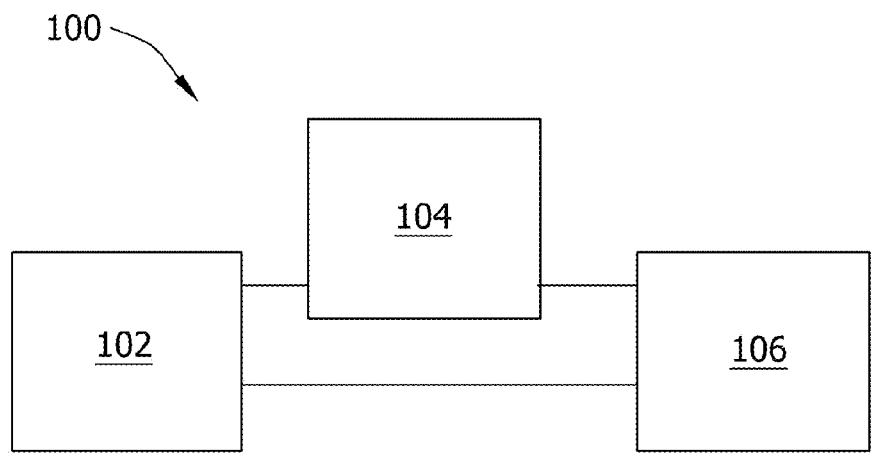
FIG. 1 is a block diagram of a system for evaluating grain size of multi-crystalline wafers.

Referring to the drawings, an exemplary evaluation system for grain size evaluation of multi-crystalline wafers is shown in FIG. 1 and indicated generally at 100. In the exemplary embodiment, system 100 includes a computing device 102, a controller 104, and an imaging apparatus 106.

System 100 evaluates grain size of one or more multi-crystalline wafers by taking multiple images of a multi-crystalline wafer under different illumination conditions. The multiple images are digitally enhanced and grain boundaries are recognized from the images. The system 100 then reports the size distribution of the grains on the solar wafer.

More specifically, in the exemplary embodiment, a multi-crystalline wafer is prepared for evaluation by etching the wafer according to any suitable etching method. In some embodiments, the wafer is etched with a solution of forty percent potassium hydroxide at eighty degrees Celsius for five minutes. In other embodiments, other solutions, temperatures, and times may be used to etch the wafer. The etched wafer is then inserted in imaging apparatus 106. Computing device 102 operates a camera (not shown in FIG. 1) in imaging apparatus 106 to capture several images of the silicon wafer. In the exemplary embodiment, computing device captures eight images of the wafer. In other embodiments, more or fewer images may be captured.

Computing device 102 also causes controller 104 to initiate a lighting sequence within imaging apparatus 106. Controller 104 may be any suitable controller including, for example, another computing device, a microcontroller, etc. Moreover, in some embodiments, system 100 does not include a separate controller 104 and the functions performed by controller 104 are performed directly by computing device 102 instead. In the exemplary embodiment, controller 104 is a microcontroller. More specifically, controller 104 is an Arduino based microcontroller. In the exemplary embodiment, controller 104 is coupled to one or more lights (not shown in FIG. 1) in imaging apparatus 106 and, in response to receiving instruction from computing device 102 to begin imaging, operates the lights to illuminate the wafer for each image to be captured. In the exemplary embodiment, controller 104 operates eight different lights in imaging apparatus 106. In the exemplary embodiment, each light is an array of six light emitting diodes (LEDs). In other embodiments, other types of lights and/or different numbers of lighting elements may be used. In the exemplary system 100, each light is operated to illuminate the multi-crystalline wafer for a different one of the captured images. In the exemplary embodiment, the lights are positioned to provide different angles and/or directions of illumination of the wafer. In other embodiments, more or fewer lights may be controlled by controller 104. Moreover, in some embodiments other lighting parameters may, additionally or alternatively, be varied. For example, a single light may be operated with different parameters, e.g. brightness, color, duration of illumination, etc., to illuminate the multi-crystalline wafer for different images.

After capturing images of the multi-crystalline wafer, computing device 102 processes the captured images. The multiple images of the wafer, each collected under a different lighting condition, are individually analyzed to find the grain boundaries in the wafer image, converted to binary images (e.g., black and white images), and stacked to form a composite image. The composite image is then analyzed by computing device 102 to identify the areas of each image surrounded by a boundary to count the number of grains in the wafer image and calculate the size of each grain. Computing device 102 then generates a report identifying the grain size of each recognized grain and the distribution of the grain size on the imaged multi-crystalline wafer.

Figure 2:
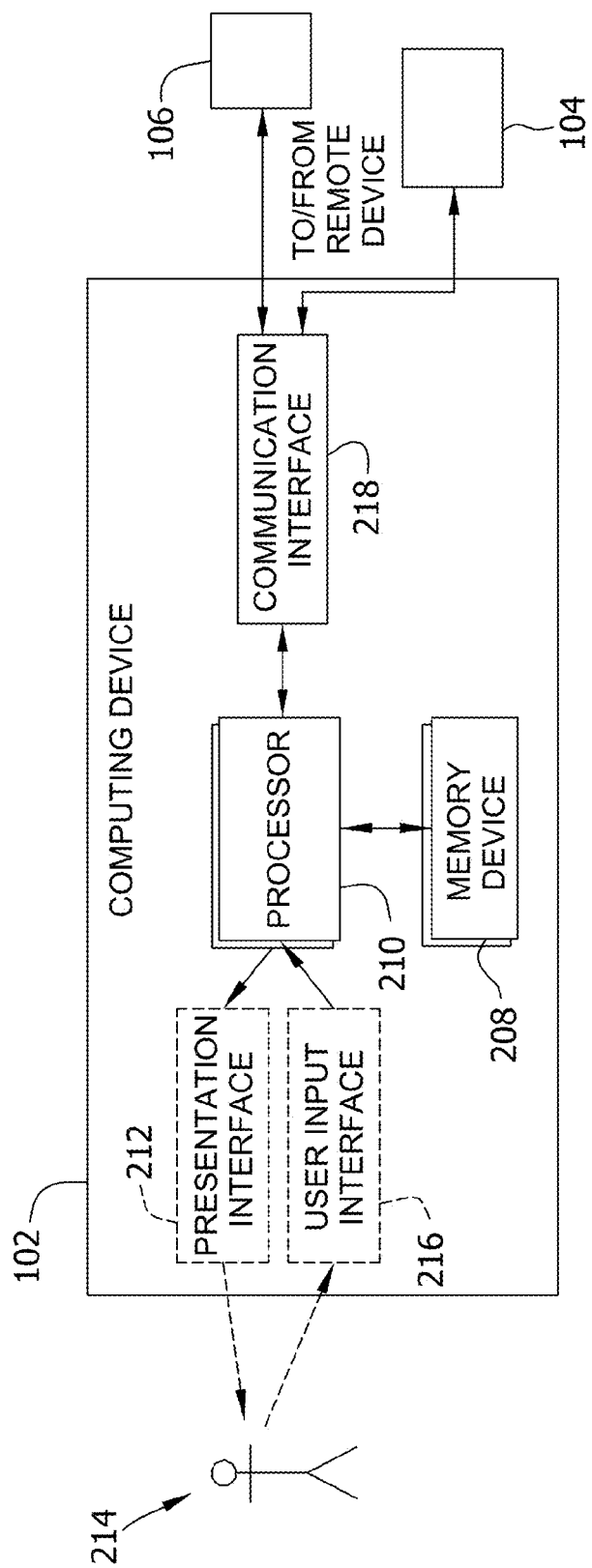
FIG. 2 is a block diagram of a computing device for use in the system shown in FIG. 1.

FIG. 2 is a block diagram of an exemplary computing device 102 that may be used with system 100. In the exemplary embodiment, computing device 102 includes a memory device 208 and a processor 210 coupled to memory device 208 for executing instructions. In some embodiments, executable instructions are stored in memory device 208. Computing device 102 performs one or more operations described herein by programming processor 210. For example, processor 210 may be programmed by encoding an operation as one or more executable instructions and providing the executable instructions in memory device 208. Processor 210 may include one or more processing units (e.g., in a multi-core configuration).

Memory device 208 is suitably one or more devices that enable information such as executable instructions and/or other data to be stored and retrieved. Memory device 208 may include one or more computer readable media, such as, without limitation, dynamic random access memory (DRAM), static random access memory (SRAM), a solid state disk, and/or a hard disk. Memory device 208 may be configured to store, without limitation, computer-executable instructions, and/or any other type of data.

In some embodiments, computing device 102 includes a presentation interface 212 that is coupled to processor 210. Presentation interface 212 presents information, such as a user interface, application source code, input events, and/or validation results to a user 214. For example, presentation interface 212 may include a display adapter (not shown in FIG. 2) that may be coupled to a display device, such as a cathode ray tube (CRT), a liquid crystal display (LCD), a light emitting diode (LED) display, an organic LED (OLED) display, and/or an "electronic ink" display. In some embodiments, presentation interface 212 includes one or more display devices. In addition to, or in the alternative, presentation interface 212 may include an audio output device (e.g., an audio adapter and/or a speaker) and/or a printer.

In some embodiments, computing device 102 includes an input interface 216. Input interface 216 may be configured to receive any information suitable for use with the methods described herein. In the exemplary embodiment, user input interface 216 is coupled to processor 210 and receives input from user 214. User input interface 216 may include, for example, a keyboard, a pointing device, a mouse, a stylus, a touch sensitive panel (e.g., a touch pad or a touch screen), a gyroscope, an accelerometer, a position detector, and/or an audio input interface (e.g., including a microphone). A single component, such as a touch screen, may function as both a display device of presentation interface 212 and user input interface 216.

Communication interface 218 is coupled to processor 210 and is configured to be coupled in communication with one or more remote devices, such as another computing device 102, a microcontroller, a remotely located memory device (not shown in FIG. 2), one or more sensors, etc. For example, communication interface 218 may include, without limitation, a serial communication adapter, a wired network adapter, a wireless network adapter, and/or a mobile telecommunications adapter. In the exemplary embodiment, communication interface 218 is coupled in communication with microcontroller 104 and imaging apparatus 106.

Figure 3:
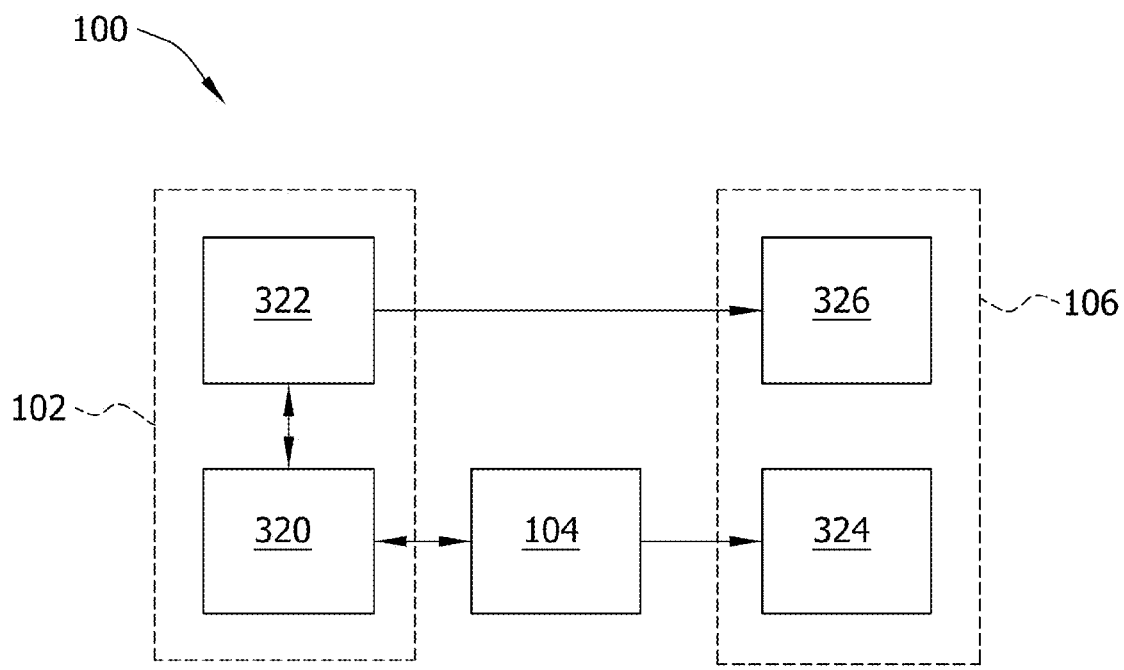
FIG. 3 is a functional block diagram of the system shown in FIG. 1.

FIG. 3 is a more detailed functional block diagram of evaluation system 100. Computing device 102 includes imaging block 320 and camera control block 322. Imaging block 320 contains code for controlling the capture of images of multi-crystalline wafers using imaging apparatus 106. In the exemplary embodiment, imaging block 320 includes any suitable image processing and analysis software. One example of suitable image processing and analysis software is Imagej, a public domain image processing and analysis program developed by the National Institutes of Health. Imaging block 320, in response to user execution, instructs controller 104 to initiate the appropriate lighting sequence of lights 324 in imaging apparatus 106 as described herein. Substantially simultaneously, imaging block 320 triggers camera control block 322. Camera control block 322 controls operation of camera 326 to capture a series of images of the multi-crystalline wafer as described herein. In the exemplary embodiment, camera control block include instructions written in the C++ computer language. In other embodiments, camera control block 322 includes any suitable instructions, including those written in languages other than C++.

Figure 4:
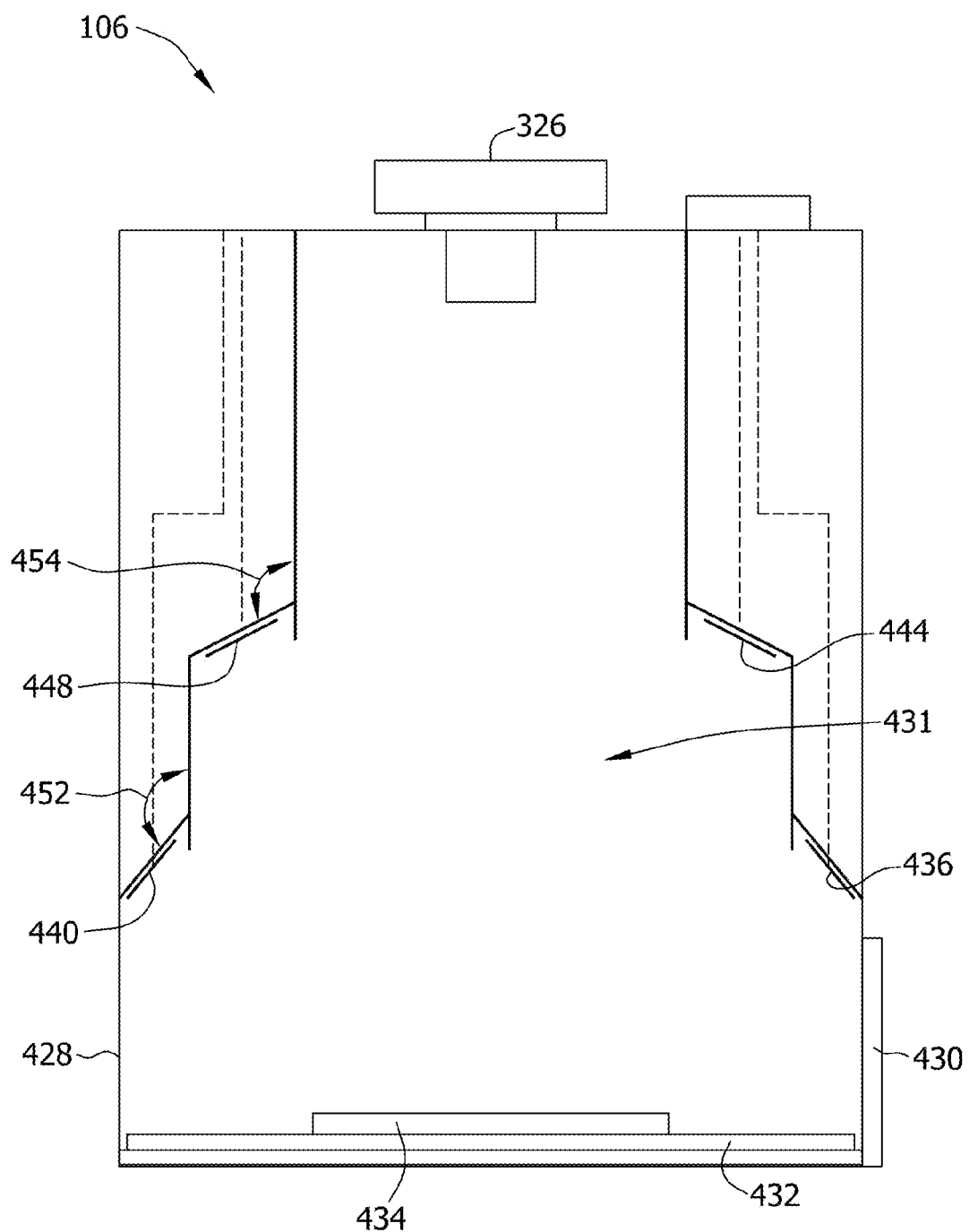
FIG. 4 is a partial section side view of an imaging apparatus for use in the system shown in FIG. 1.
Figure 5:
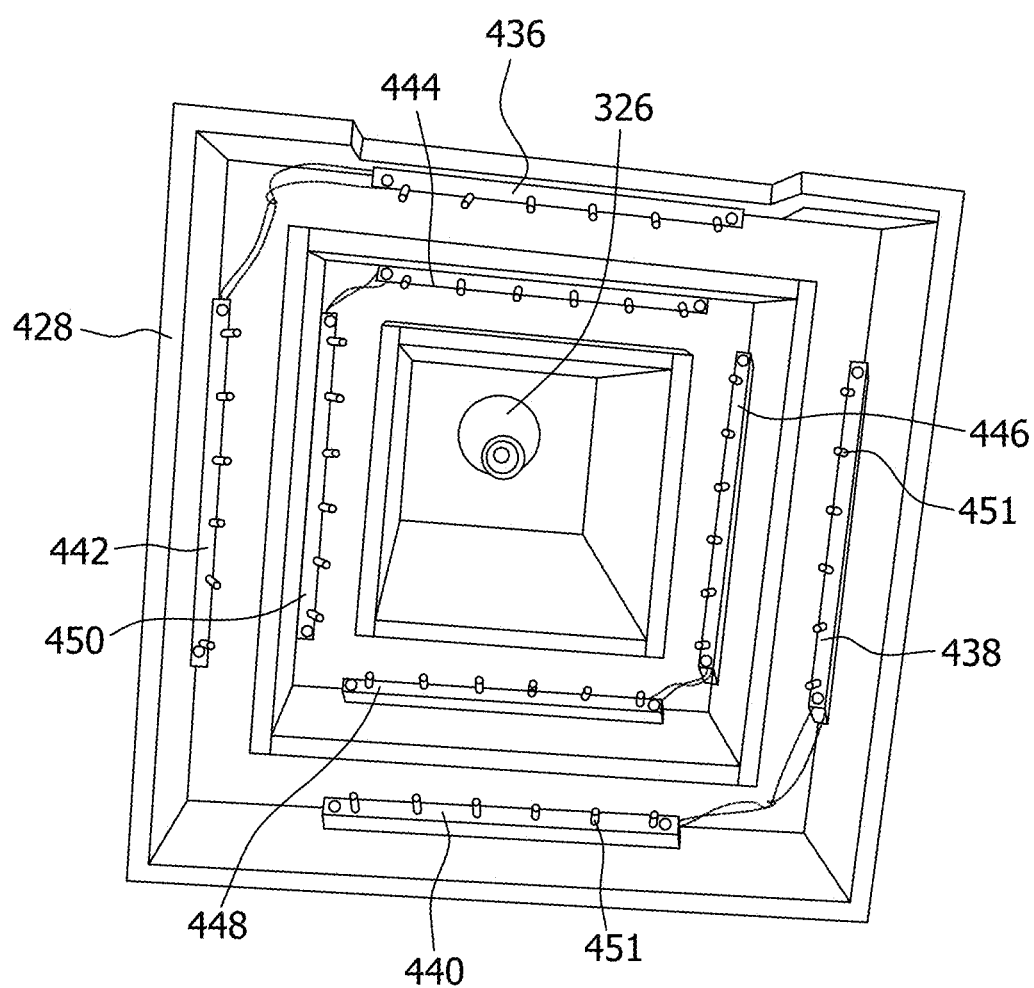
FIG. 5 is a bottom perspective view of the imaging apparatus shown in FIG. 4.

FIGS. 4 and 5 illustrate imaging apparatus 106. Imaging apparatus 106 includes a housing 428. As shown in FIG. 4, a door 430 is coupled housing 428. Door 430 is configured to provide access to an interior 431 of imaging apparatus 106. In the exemplary embodiment, door 430 is slidably coupled to housing 428. In other embodiments, door 430 may be coupled to housing by any other suitable method including, for example, by hinges. A sample tray 432 is slidably coupled to housing 428 to slide in and out of the interior of imaging apparatus 106 to receive a wafer for inspection. In other embodiments, sample tray 432 is not attached to housing 428 or is coupled to housing 428 by other suitable connection. In still other embodiments, imaging apparatus 106 does not include a sample tray and the wafer is inserted directly into imaging apparatus 106. In some embodiments, a wafer is fed into housing 428 of imaging apparatus 106 via a conveyer belt (not shown). An example wafer 434 is shown on sample tray 432 in FIG. 4.

Camera 326 is coupled to imaging apparatus 106 to capture images of wafer 434. Camera 326 is coupled to housing 428 a fixed distance from sample tray 432 and positioned to capture an image of wafer 434. In the exemplary embodiment, camera 326 is a digital grayscale camera. More particularly, camera 326 has a five megapixel resolution and a universal serial bus (USB) interface. In other embodiments any other suitable camera may be used including, for example, a color camera, a camera without a USB interface, etc.

As described above, in the exemplary embodiment imaging apparatus 106 includes lights 324 to illuminate wafer 434. Lights 324 include eight arrays 436, 438, 440, 442, 444, 446, 448, and 450 of LEDs. Each array 436, 438, 440, 442, 444, 446, 448, and 450 include six LEDs 451. In the exemplary embodiment, LEDs 451 are white light LEDs with a diffused lens. In other embodiments, LEDs emitting other spectra of light may be used. Additionally, LEDs with a clear, i.e. not diffused, lens may be used in other embodiments.

Arrays 436, 438, 440 and 442 are mounted to housing 428 at a first level a substantially fixed distance from tray 432 (and accordingly from wafer 434). Arrays 444, 446, 448, and 450 are mounted to housing 428 at a second level a substantially fixed distance from tray 432. The second level is farther away from sample tray 432, and wafer 434, than the first level. Accordingly, the arrays 444, 446, 448, and 450 are mounted farther away from wafer 434 than arrays 436, 438, 440 and 442.

At the first level the housing 428 defines a first angle 452 relative to vertical different than a second angle 454 that it defines at the second level. Accordingly, arrays 436, 438, 440 and 442 are oriented at first angle 452 relative to vertical, while arrays 444, 446, 448, and 450 are oriented at second angle 454 relative to vertical. First angle 452 is greater than second angle 454. In the exemplary embodiment, first angle 452 is about one hundred and fifty degrees and second angle 454 is about one hundred and twenty degrees. In other embodiments, first and second angles 452, 454 may have other values. The described arrangement of lights 324 results in light from arrays 436, 438, 440 and 442 illuminating wafer 434 with light incident at a different angle than light originating from arrays 444, 446, 448, and 450. Moreover, light from each array in a level, e.g., arrays 436, 438, 440 and 442 in the first level, is directed at wafer 434 from a different direction. As best seen in FIG. 5, for example, each of arrays 436, 438, 440, and 442 extends approximately perpendicular to its adjacent arrays. Thus, each array in a particular level will illuminate wafer 434 from a different direction, but at a same distance and a same angle. In operation, controller 104 illuminates one array 436, 438, 440, 442, 444, 446, 448, and 450 for each image of wafer 434 to be captured. The exemplary embodiment, therefore, captures eight images of each wafer 434, with each image illuminated by a different one of arrays 436, 438, 440, 442, 444, 446, 448, and 450.

In the exemplary embodiment, imaging apparatus 106 approximately three hundred millimeters by long by three hundred millimeters wide by five hundred millimeters high. The exemplary imaging apparatus 106 is large enough to receive and image wafers up to about one hundred and fifty six millimeters by one hundred and fifty six millimeters. In other embodiments, imaging apparatus 106 may made smaller or larger. Housing 428 may be made proportionally smaller or larger as desired. Further, changing the size of imaging device 106 may change the required light output from arrays 436, 438, 440, 442, 444, 446, 448, and 450 and/or spatially limit the number of LEDs that may be included in arrays 436, 438, 440, 442, 444, 446, 448, and 450. Accordingly, the number of LEDs in each array 436, 438, 440, 442, 444, 446, 448, and 450 may be decreased or increased as imaging apparatus 106 is decreased or increased in size. Alternatively, or additionally, the intensity of the LEDs in arrays 436, 438, 440, 442, 444, 446, 448, and 450 may be adjusted along with the size of imaging apparatus 106.

Figure 6:
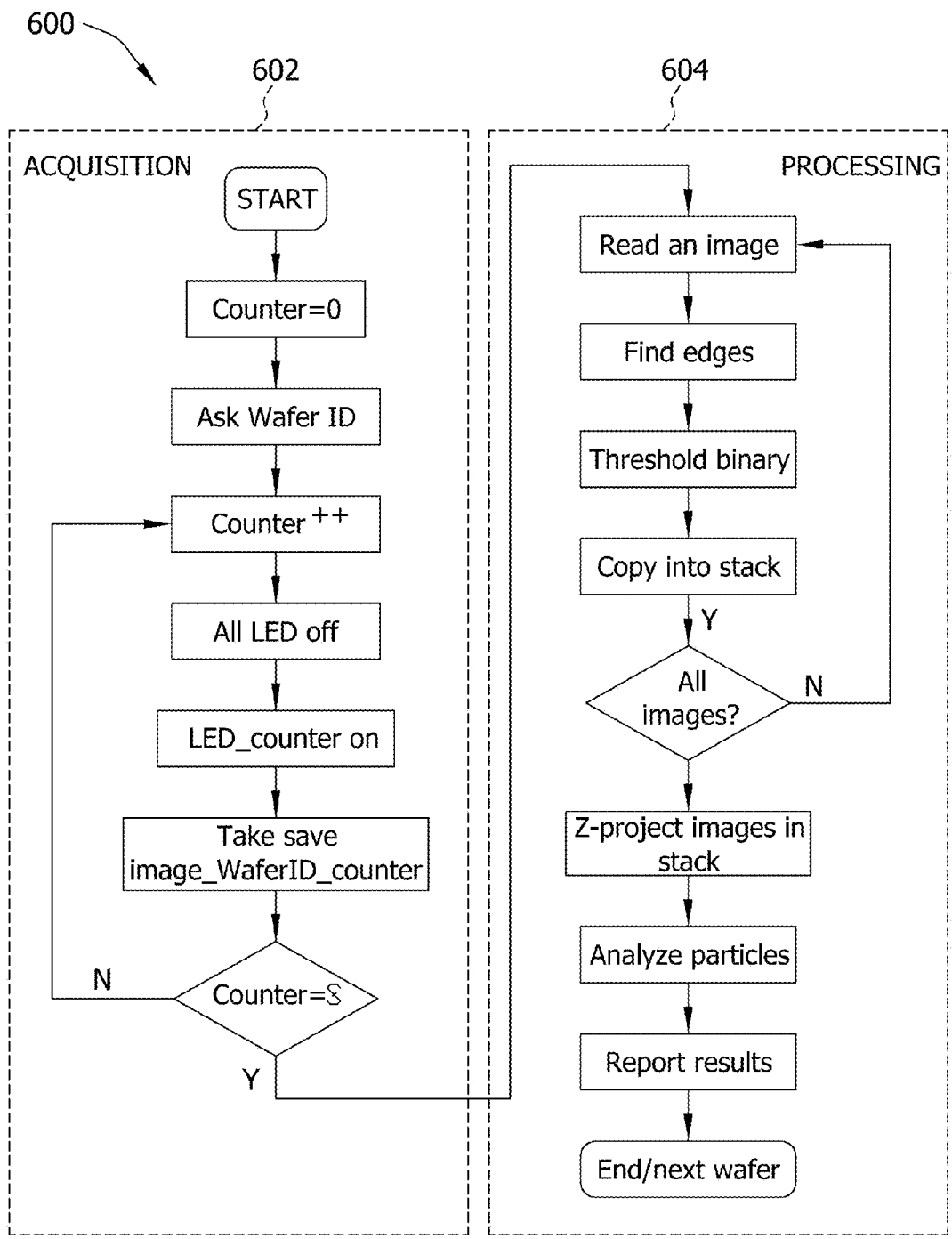
FIG. 6 is a flow diagram of a method of evaluating multi-crystalline wafers using the system shown in FIG. 1.

FIG. 6 is a flow diagram of an operation 600 of evaluation system 100. Operation 600 is subdivided into an image acquisition process 602 and a processing process 604. During the acquisition process 602, which begins after a wafer is inserted into imaging apparatus 106, a counter is initially set to zero. Before an image is captured, the counter is incremented and all arrays 436, 438, 440, 442, 444, 446, 448, and 450 are turned off. The array to which the current counter number is assigned is instructed, by computing device 102 via controller 104, to turn on and an image is acquired and saved. If the counter is less than or equal to eight, the counter increments and the process is repeated.

When all eight images have been acquired, the processing process 604 begins. Each captured image is individually read and processed. Each image is examined by computing device 102 to determine, for each contrast change in the grayscale image, whether or not the contrast change exceeds a defined threshold to be identified as a grain boundary. After the grain boundaries have been identified for an image, the grayscale image is converted into a binary image (i.e., a black and white image) that preserves only the grain boundaries identified in the image. Each binary image is copied into a stack and the process repeats until all images of a particular wafer have been processed and copied into the stack. The stack of images is then projected down to a single composite image. The stack may be projected using any suitable projection method including, for example, a sum projection, a maximum projection, an average projection, a standard deviation projection, etc. Computing device 102 then analyzes the composite image to identify and calculate the size of the grains shown in the composite image. A grain is identified as an area fully enclosed by the identified boundary lines. After the image is analyzed, a report is generated by computing device 102. The report indicates the size of each identified grain and the distribution of the grain sizes on the wafer.

Figure 7:
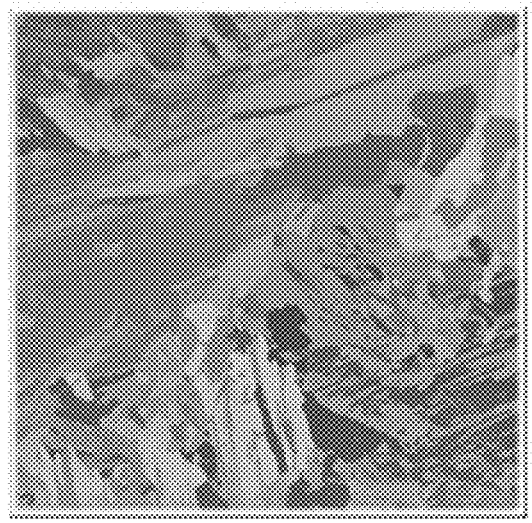
FIG. 7 is an image of a multi-crystalline silicon wafer captured using the system shown in FIG. 1.
Figure 8:
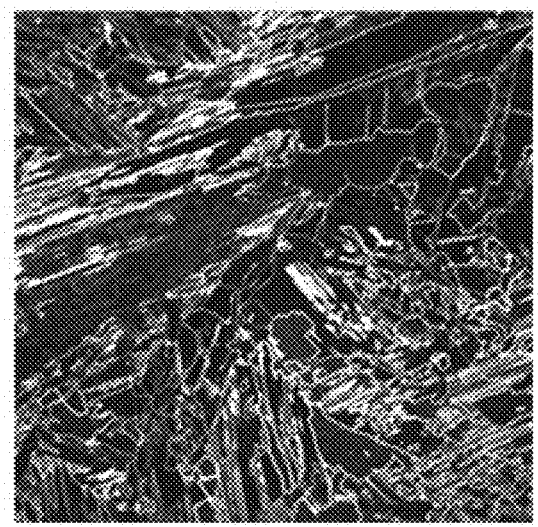
FIG. 8 is the image shown in FIG. 7 after initial processing by the system in FIG. 1.
Figure 9:
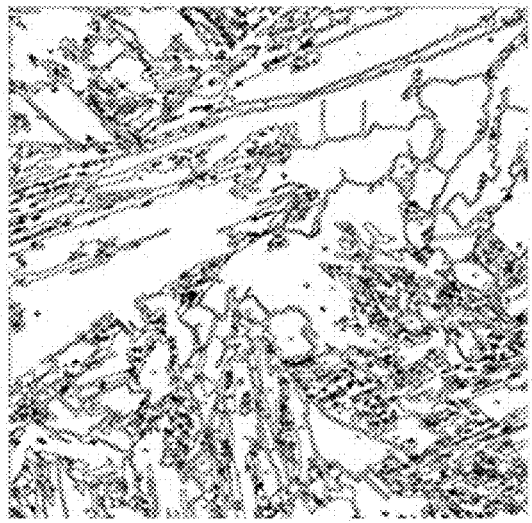
FIG. 9 is the image in FIG. 8 after further processing by the system shown in FIG. 1.

FIGS. 7-9 are exemplary images produced by evaluation system 100. FIG. 7 is an optical image (a single image) of a multi-crystalline wafer captured using imaging apparatus 106. FIG. 8 shows the image (a single image) in FIG. 7 after processing and conversion to a binary image as described above. FIG. 9 shows a composite image including the image in FIG. 8 and other images of the same multi-crystalline wafer stacked and projected as described above. The image in FIG. 9 is color inverted (or otherwise suitably inverted, such as to dark lines) and the grain boundaries, and thus the grains themselves, are clearly identified.

The multi-crystalline wafer evaluation methods and systems described herein permit automated evaluation of a wafer. Moreover, the systems and methods provide for automated acquisition and processing of images of a wafer to be evaluated. Identification of grains, determination of grain size, and determination of distribution of grains is performed automatically by a computing device. Hence the methods and systems described herein may reduce human error and delays, while permitting fast, reliable, and inexpensive evaluation of multi-crystalline wafers.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A system for evaluating a multi-crystalline wafer comprising:
   an imaging apparatus; and
   a computing device coupled to the imaging apparatus, the computing device comprising a processor and a non-transitory computer readable medium coupled in communication with the processor and containing instructions that, when executed by the processor, cause the processor to:
   capture a plurality of images of the multi-crystalline wafer in the imaging apparatus, at least three images of the plurality of images illuminated in the imaging apparatus in accordance with different lighting parameters;
   stack and project the plurality of images to generate a composite image to display at least one enhanced boundary of one or more grains of the multi-crystalline wafer;
   analyze the composite image to identify the one or more grains of the multi-crystalline wafer based at least in part on the at least one enhanced boundary; and
   generate a report based on the analysis of the composite image.

2. A system according to claim 1, wherein the imaging apparatus comprises an imaging device and a plurality of lights positioned to illuminate the multi-crystalline wafer in the imaging apparatus.

3. A system according to claim 2, wherein the plurality of lights comprise at least a first light oriented to illuminate the multi-crystalline wafer in the imaging apparatus from a first angle and a second light oriented to illuminate the multi-crystalline wafer from a second angle different than the first angle.

4. A system according to claim 3, wherein the plurality of lights consists of four lights oriented to illuminate the multi-crystalline wafer from the first angle and four lights oriented to illuminate the multi-crystalline wafer from the second angle.

5. A system according to claim 3, further comprising a third light, wherein the first light is positioned to illuminate the multi-crystalline wafer from a first direction and the third light is positioned to illuminate the multi-crystalline wafer from a second direction different than the first direction.

6. A system according to claim 2, wherein the plurality of lights comprises at least a first light positioned to illuminate the multi-crystalline wafer in the imaging apparatus from a first height above the multi-crystalline wafer and a second light positioned to illuminate the multi-crystalline wafer from a second height above the multi-crystalline wafer different than the first height.

7. A system according to claim 6, wherein the first light is oriented to illuminate the multi-crystalline wafer in the imaging apparatus from a first angle and the second light is oriented to illuminate the multi-crystalline wafer from a second angle different than the first angle.

8. A system according to claim 6, wherein the plurality of lights consists of four lights positioned at the first height and four lights positioned at the second height.

9. A system according to claim 6, further comprising a third light, wherein the first light is positioned to illuminate the multi-crystalline wafer from a first direction and the third light is positioned to illuminate the multi-crystalline wafer from a second direction different than the first direction.

10. A system according to claim 2 wherein the plurality of lights comprises at least a first light positioned to illuminate the multi-crystalline wafer in the imaging apparatus from a first direction and a second light positioned to illuminate the multi-crystalline wafer from a second direction different than the first direction.

11. A system according to claim 2, wherein the plurality of lights comprise light emitting diodes.

12. A system according to claim 1, wherein the instructions further cause the processor to analyze and process each image of the plurality of images to determine one or more boundaries of one or more grains of the multi-crystalline wafer.

13. A system according to claim 2, further comprising a controller coupled in communication with the computing device and the plurality of lights, the controller configured to control a sequence of illumination of the multi-crystalline wafer in the imaging apparatus.

14. A system according to claim 2, wherein the non-transitory computer readable medium contains instructions that, when executed by the processor, cause the processor to convert the plurality of images to binary images.

15. A system according to claim 2, wherein the non-transitory computer readable medium contains instructions that, when executed by the processor, cause the processor to determine a size of each of the one or more grains of the multi-crystalline wafer identified in the composite image.

16. A method for use in evaluating a multi-crystalline wafer comprising:
    illuminating the multi-crystalline wafer according to a plurality of lighting parameters;
    capturing a plurality of images of the multi-crystalline wafer, wherein the multi-crystalline wafer is illuminated according to a different one of the plurality of lighting parameters in at least three images of the plurality of images;
    stacking and projecting the plurality of images to generate a composite image to display at least one enhanced boundary of one or more grains of the multi-crystalline wafer;
    analyzing the composite image to identify the one or more grains of the multi-crystalline wafer based at least in part on the at least one enhanced boundary; and
    generating a report based on the analysis of the composite image.

17. A method according to claim 16, wherein illuminating the multi-crystalline wafer according to a plurality of lighting parameters comprises illuminating the plurality of lighting parameters from at least two different angles of illumination.

18. A method according to claim 16, wherein illuminating the multi-crystalline wafer according to a plurality of lighting parameters comprises illuminating the plurality of lighting parameters from at least two different heights of illumination.

19. A method according to claim 16, wherein illuminating the multi-crystalline wafer according to a plurality of lighting parameters comprises illuminating the plurality of lighting parameters from at least two different directions of illumination.

20. A method according to claim 16, wherein analyzing the composite image further comprises determining a size of each of the one or more grains of the multi-crystalline wafer identified in the composite image.

\* \* \* \* \*